United States Patent
Gibson (12) 
(10) Patent No.: US 6,416,177 B1
(45) Date of Patent: Jul. 9, 2002

(54) TRANSPARENT FILM ASSEMBLY FOR A PROTECTIVE GOGGLE WITH A RENEWABLE VIEWING SURFACE

(75) Inventor: George N. Gibson, Ketchum, ID (US)

(73) Assignee: Smith Sport Optics, Inc., Ketchum, ID (US)

( * ) Notice: Subject to any disclaimer, the term of this patent is extended or adjusted under 35 U.S.C. 154(b) by 0 days.

(21) Appl. No.: 09/788,306

(22) Filed: Feb. 16, 2001

(51) Int. Cl.[7] .............................. G02C 9/00; G02C 1/00; A61F 9/02
(52) U.S. Cl. ........................ 351/41; 351/47; 351/158; 2/438
(58) Field of Search ........................... 351/41, 47, 48, 351/57, 58, 158; 2/438, 435, 442

(56) References Cited

U.S. PATENT DOCUMENTS

| | | | |
|---|---|---|---|
| 3,603,672 A | * 9/1971 | Bastide | 351/47 |
| 3,945,044 A | 3/1976 | McGee et al. | 2/14 H |
| 4,076,373 A | 2/1978 | Moretti | 350/61 |
| 4,138,746 A | 2/1979 | Bergmann | 2/424 |
| 4,428,081 A | 1/1984 | Smith | 2/438 |
| 4,455,687 A | 6/1984 | Johansson | 2/424 |
| 4,455,689 A | 6/1984 | Boyer | 2/434 |
| 4,528,701 A | 7/1985 | Smith | 2/438 |
| 4,563,065 A | 1/1986 | Kreissl | 351/86 |
| 4,716,601 A | 1/1988 | McNeal | 2/434 |
| 6,047,412 A | * 4/2000 | Wilson, II et al. | 2/438 |

* cited by examiner

Primary Examiner—Huy Mai
(74) Attorney, Agent, or Firm—Dorsey & Whitney LLP (57) ABSTRACT

The invention is directed towards an apparatus for mounting and retaining a protective film that shields the surface of protective lens from vision-impairing accumulations of dust, mud, or other opaque materials. More particularly, the present invention is directed to a film retaining apparatus for use with a goggle with a renewable protective surface that offers increased film interchangeability. In one embodiment, the apparatus is comprised of spool for retaining the protective film having a spool end that is adapted to engage a film advancing mechanism in a first group of goggles, and an opposing spool end adapted to engage a film advancing mechanism in a second group of goggles. In another embodiment, the spool ends are removably coupled to a center cylindrical spool portion that retains the film to advantageously permit various engagement configurations to be used.

83 Claims, 4 Drawing Sheets

TRANSPARENT FILM ASSEMBLY FOR A PROTECTIVE GOGGLE WITH A RENEWABLE VIEWING SURFACE

TECHNICAL FIELD

This invention relates generally to the shielding of a protective lens used for vision protection, and more particularly, to the shielding of a lens of a protective goggle from vision-impairing accumulations of dust, mud, or other opaque materials.

BACKGROUND OF THE INVENTION

Goggles are employed in a wide variety of activities for vision protection, and the type of goggle used generally varies in accordance with the activity, and the environmental conditions encountered. In some activities, the lens of the goggle is subjected to accumulations of vision-impairing materials, such as dust, mud or ice, that must be cleared from the lens of the goggle with a minimum of distraction to the wearer. For example, off-road motorcycle or bicycle racers frequently wear goggles while racing to avoid eye injuries stemming from the relatively large amount of mud or other debris that are thrown aloft from the track surface. As a result, mud, water or other debris frequently covers the lenses of the goggles, impairing the vision of the wearer. To remove the obscuring matter from the lens surface, the wearer generally uses a hand or a forearm to wipe a portion of the obscuring matter from the lens surface. A shortcoming inherent in this approach is that the lens may remain partially or even wholly obscured after wiping, and that the wearer's attention is distracted from the activity during the wiping operation, which may seriously compromise the safety of the wearer.

In order to alleviate the shortcomings inherent in the practice of wiping the obscuring material from the lens surface of the goggles, a plurality of stacked transparent flexible sheets have been positioned in front of a conventional goggle lens. When sufficient debris covers the surface of an exposed transparent flexible sheet, so that vision is impaired, the sheet may be removed by the wearer to obtain a clean goggle surface. Examples of devices of this type are disclosed in U.S. Pat. No. 3,945,044 to McGee, et al., U.S. Pat. No. 4,076,373 to Moretti, U.S. Pat. No. 4,138,746 to Bergmann, U.S. Pat. No. 4,455,687 to Johansson, U.S. Pat. No. 4,455,689 to Boyer, U.S. Pat. No. 4,563,065 to Kreissl, and U.S. Pat. No. 4,716,601 to McNeal. A significant disadvantage associated with the approach disclosed in the foregoing patents is that the number of superimposed transparent flexible sheets that may be positioned on the goggle is limited, since optical attenuation and distortion of the field of vision increases as the number of transparent sheets is increased. Accordingly, if the wearer is exposed to lens-occluding conditions for a protracted period of time, a sufficient number of transparent sheets may not be available to the wearer. An additional disadvantage associated with the approach disclosed in the foregoing patents is that the removed transparent flexible sheets are generally not retained by the user, and are discarded immediately following removal. As a result, the removed sheets may constitute a waste disposal problem in the area in which they are used. Additionally, in some environments, such as the above-described off-road race environment, or in other similar environments, the release of the removed sheets may constitute a safety hazard by inadvertently striking other participants following release of the removed sheet.

Figure 1:
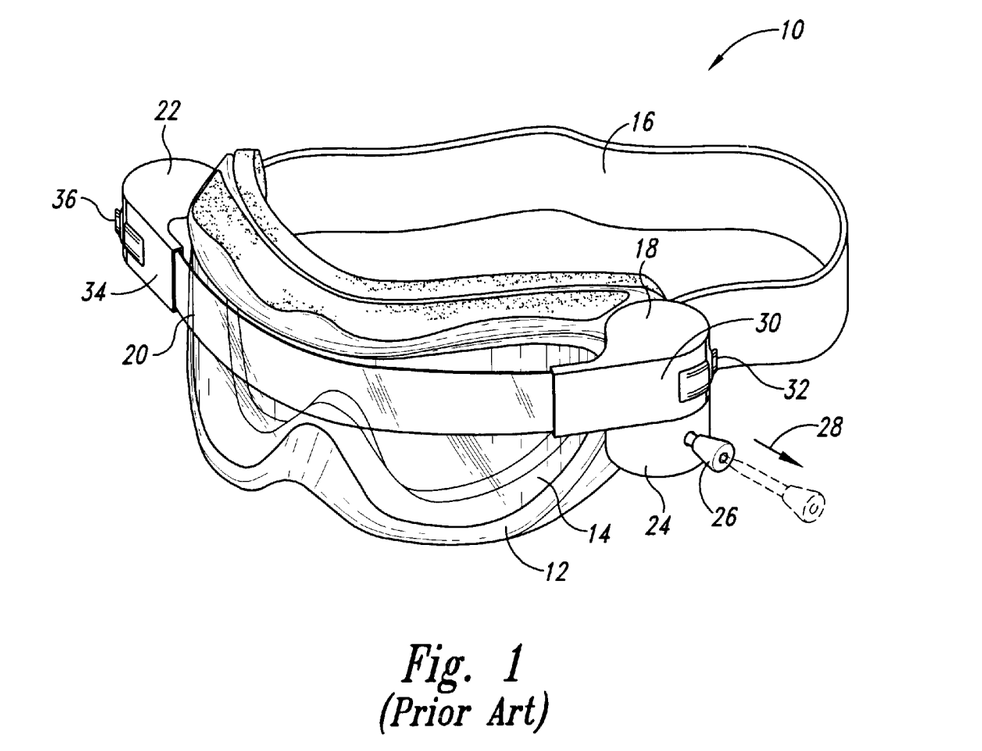
FIG. 1 is an isometric view of a protective goggle with a renewable protective surface according to the prior art.

An additional solution to the problem of vision impairment resulting from accumulations of vision obscuring matter on the surface of a goggle is disclosed in U.S. Pat. Nos. 4,428,081 and 4,528,701 Smith, which are incorporated by reference in the present application. Briefly, and in general terms, the Smith patents disclose a goggle assembly having a pair of rollers positioned on opposite sides of a goggle that support an elongated, rectangular-shaped length of a transparent film in front of a permanent goggle lens. When vision obscuring matter accumulates on the permanent lens and the transparent film in front of the lens, the user may advance the transparent film across the permanent lens surface to remove an obscured portion of the transparent film from the field of view of the wearer. A goggle 10 of the type disclosed in the Smith patents is shown in FIG. 1. The goggle 10 includes a frame 12 that is comprised of a resilient material that holds a semi-rigid, transparent lens 14. An elastic head strap 16 is attached to the frame 12 that permits the goggle 10 to be firmly secured onto the head of the wearer. Attached to the frame 12 and adjacent to one end of the lens 14 is a supply magazine 22 containing a roll (not shown) of transparent film 20 that is tightly wound onto a supply spool (not shown). The supply spool is installed in the supply magazine 22 by releasing the resilient catch 36 on the supply magazine cover 34. When the transparent film 20 is installed in the supply magazine 22, the film 20 extends from the supply magazine 22 across the surface of the lens 14 to a take up magazine 18, thus forming a protective surface across the surface of the lens 14. The take up magazine 18 has a take up spool (not shown) that is structured to receive the film 20 once it has become unusable. The take up magazine 18 has a take up magazine cover 30 that is attached to the take up magazine 18 by a resilient catch 32. The take up magazine also has a film advancing mechanism 24 with a knob 26 that is attached to a cord (shown in phantom outline) to manually advance a length of the transparent film 20 across the lens surface. The film advancing mechanism 24 is manually actuated by grasping and pulling the knob 26 in the direction 28 to advance a new length of transparent film 20 across the front surface of the lens 14.

Although the foregoing prior art device is a significant improvement over the other prior art devices previously discussed, the film transport means constitutes a shortcoming of the foregoing device. In particular, the take up spool must be lockably engaged to the film advancing mechanism 24 in order to apply a torque to the take up spool, thus tensioning the film 20 to remove the used portion of the film 20 from the surface of the lens 14, and to withdraw a new portion of the film 20 from the supply magazine 22. To date, the film advancing mechanisms 24 of the goggle 10 have used a variety of spool engagement means that has caused the take up spools to be generally not interchangeable between goggles of different model types. As a result, a user may inadvertently purchase the wrong spool for the user's goggles, and sellers of the spools must stock several varieties of the spools.

SUMMARY OF THE INVENTION

The invention is directed towards an apparatus for mounting and retaining a protective film that shields the surface of a protective lens from vision-impairing accumulations of dust, mud, or other opaque materials. More particularly, the present invention is directed to a film retaining apparatus for use with a goggle with a renewable protective surface that offers increased film interchangeability. In one aspect of the invention, the apparatus is comprised of spool for retaining the protective film having a spool end that is adapted to engage a film advancing mechanism in a first group of goggles, and an opposing spool end adapted to engage a film advancing mechanism in a second group of goggles. In a further aspect, the spool ends are removably coupled to a center cylindrical spool portion that retains the film to advantageously permit various engagement configurations to be used.

DETAILED DESCRIPTION OF THE INVENTION

The present invention is generally directed to an apparatus for mounting and retaining a protective film that shields the surface of a protective lens from vision-impairing accumulations of dust, mud, or other opaque materials. More particularly, the present invention is directed to a film retaining apparatus for use with a goggle with a renewable protective surface that offers increased film interchangeability. Many of the specific details of certain embodiments of the invention are presented in the following description and in FIGS. 2–11 to provide a thorough understanding of such embodiments. One skilled in the art will understand, however, that the present invention may have additional embodiments, or that the present invention may be practiced without several of the details described in the following description. For example, one skilled in the art will understand that in the following discussion, the description of various details of the take-up spool may equally apply to the supply spool as well.

Figure 2:
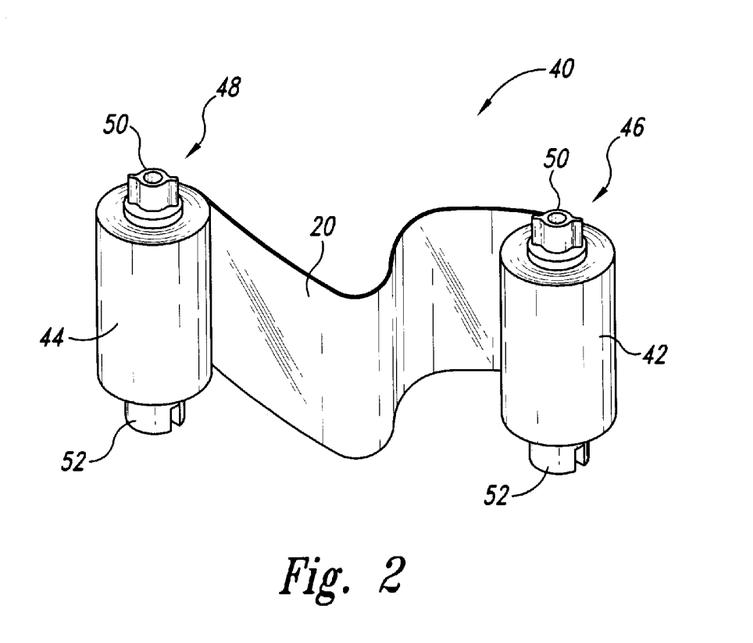
FIG. 2 is an isometric view of a transparent film assembly according to an embodiment of the invention.

FIG. 2 is an isometric view of a transparent film assembly 40 according to an embodiment of the invention. The assembly 40 is comprised of a take-up spool 46 and a supply spool 48 having a length of a transparent protective film 20 disposed therebetween. The take-up spool 46 is comprised of a cylindrical shaft with opposing ends 50 and 52 that are each adapted to lockably engage an engagement member in the film advancing mechanism 24 (as shown in FIG. 1), which will be discussed in greater detail below. The take-up spool 46 is structured to permit a used portion 42 of the transparent protective film 20 to be wound circumferentially around the axis of the spool 46 to compactly store the used portion 42 when the spool 46 is positioned within the take-up magazine 30 (as shown in FIG. 1). The supply spool 48 is similarly comprised of a cylindrical shaft having opposing ends 50 and 52 that is structured to permit an unused portion 44 of the transparent protective film 20 to be wound circumferentially around the axis of the spool 48 to compactly store the unused portion 44 when the spool 48 is positioned within the supply magazine 34 (as shown in FIG. 1). Although FIG. 2 shows the supply spool 48 and the take-up spool 46 having significant portions 44 and 42 of the transparent protective film 20 wound circumferentially around the spools 48 and 46, when a replacement film 20 is positioned in the supply magazine 22, the supply spool 48 retains substantially all of the film 20, with an end of the film 20 being attached to the take-up spool 46 by fastening the end of the film 20 to the spool 46 using an adhesive, or by positioning the film in an interlocking groove in the spool 46 (not shown). When vision-impairing matter is removed from the lens surface, the film 20 is sequentially advanced from the supply spool 48 to the take-up spool 46. Ultimately, the sequential advancement of the film 20 culminates in the removal of all of the film 20 from the spool 48. At this point, the take-up spool 46, which now contains substantially the entire length of the film 20, is removed from the take-up magazine 18 and discarded. The empty supply spool 48 is then removed from the supply magazine 22 and placed in the take-up magazine 18 to receive a new used portion 42 of the film 20.

Figure 3:
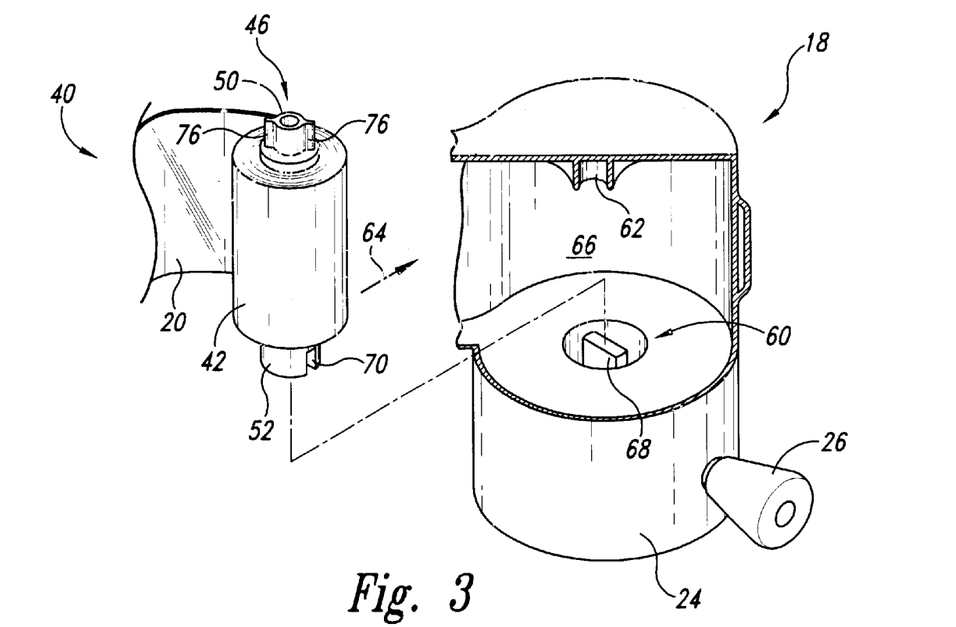
FIG. 3 is a partial isometric view of the transparent film assembly according to an embodiment of the invention being installed into a supply magazine.

Turning now to FIG. 3, a partial isometric view of the transparent film assembly 40 according to an embodiment of the invention is shown just prior to insertion of the take-up spool 46 into the take-up magazine 18. For clarity, the take-up magazine cover 30 (as shown in FIG. 1) that is normally positioned on the frontal portion of the take-up magazine 18 has been removed in order to better illustrate the present embodiment. As shown in FIG. 3, the take-up spool 46 may be positioned within the take-up magazine 18 by moving the spool 46 in the direction 64 and into the internal recess 66 of the take-up magazine 18 while allowing the take-up spool end 52 to engage the film advance drive member 60 within the magazine 18. The take-up spool end 52 has a slot 70 formed therein that has a generally rectangular cross sectional shape configured to positively engage a tab 68 that projects upwardly from the member 60. When the tab 68 is properly engaged with the spool end 52, a torque may be positively transferred to the spool 52 from the advance member 60 when the film advance mechanism 24 is manually actuated. The opposing take-up spool end 50 is inserted into the slot 62 within the magazine 18 in order to properly align and capture the take-up spool 46 within the magazine 18.

Figure 4:
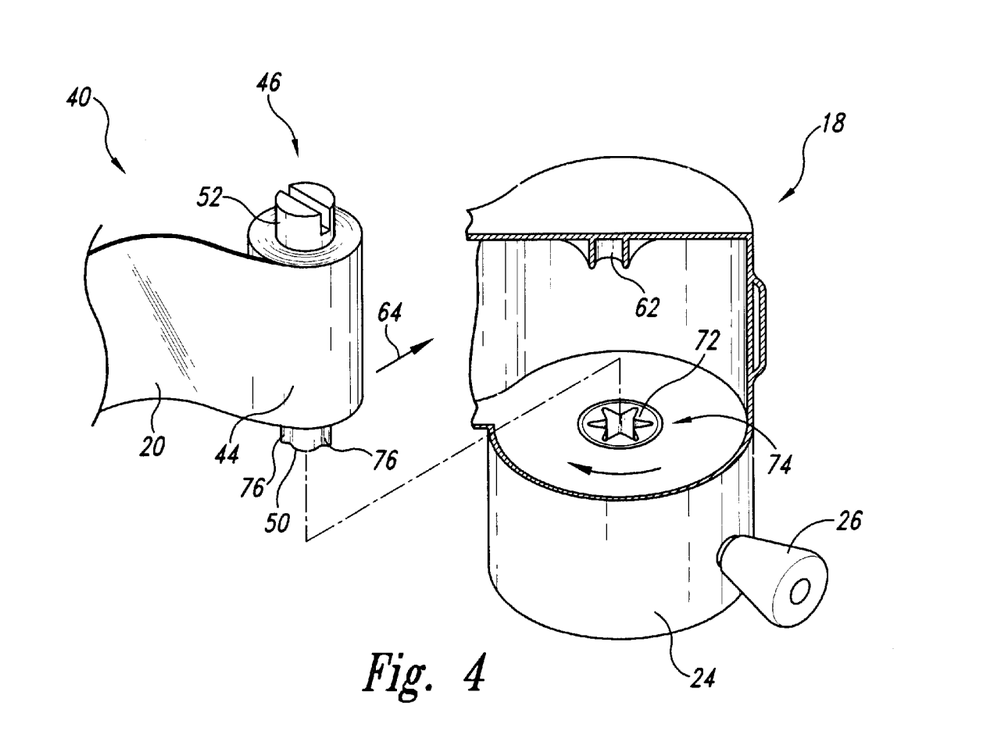
FIG. 4 is a partial isometric view of the transparent film assembly according to an embodiment of the invention being installed into a different supply magazine.

With reference now to FIG. 4, a partial isometric view of the transparent film assembly 40 according to the same embodiment is shown just prior to insertion of the take-up spool 46 into the take-up magazine 18. In this view, the take-up spool 46 is inverted relative to the view shown in FIG. 3, so that the take-up spool end 52 is directed generally upwardly and away from the film advance mechanism 24. The take-up magazine 18 that is depicted in FIG. 4 has film advance drive member 74 within the magazine 18 that is comprised of an internal involute spline 72. The spool 46 is positioned within the magazine 18 by moving the spool 46 in the direction 64 so that the radially projecting engagement tabs 76 (as best seen in FIG. 3) are positioned within the recess of the internal spline 72 to positively rotationally engage the spool 46. The opposing take-up spool end 52 is inserted into the slot 62 within the magazine 18 in order to properly align and capture the take-up spool 46 within the magazine 18.

Figure 5:
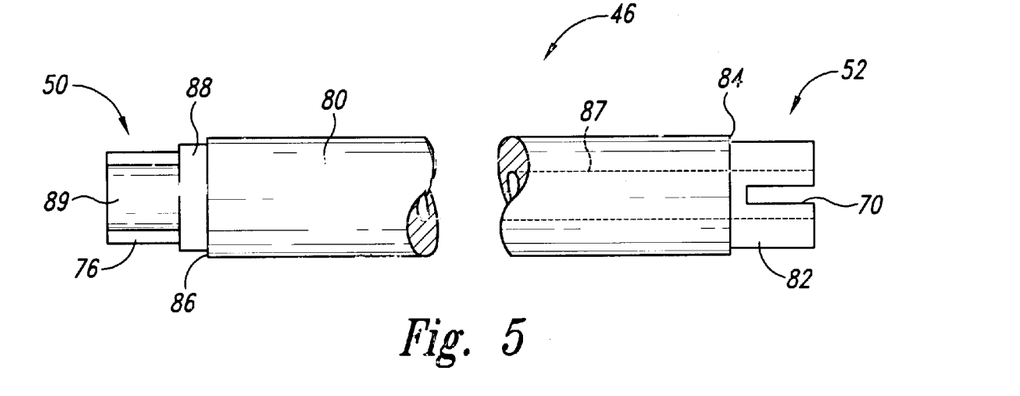
FIG. 5 is a side view of a spool for retaining the transparent film according to an embodiment of the invention.
Figure 6:
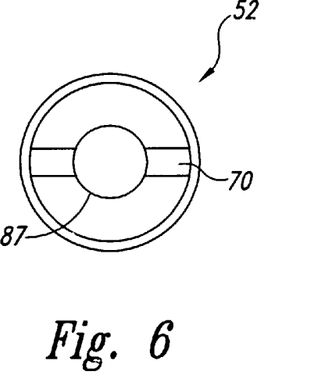
FIG. 6 is an end view of a spool for retaining the transparent film according to an embodiment of the invention.
Figure 7:
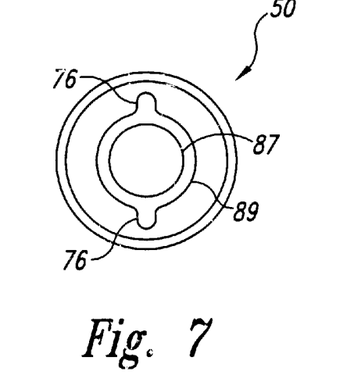
FIG. 7 is an end view of a spool for retaining the transparent film according to an embodiment of the invention.

With reference now to FIGS. 5, 6 and 7, the take-up spool will be described in further detail. As best seen in FIG. 5, the take-up spool 46 is comprised of a cylindrical center portion 80 onto which layers of the transparent film 20 are wrapped (as shown in FIGS. 2, 3 and 4). The center portion 80 preferably has an approximate diameter of between about 0.2 inches to about 0.3 inches. A central bore 87 optionally extends through the entire length of the take-up spool 46 and has an approximate diameter that ranges between about 0.1 inches to about 0.15 inches. With reference now to FIGS. 5 and 6, a first end 52 of spool 46 has a cylindrical portion 82 that abuts the central portion 80 at a shoulder 84. The cylindrical portion 82 may have a diameter that ranges from approximately about 0.18 inches to approximately about 0.27 inches, and a length of approximately about 0.080 inches to approximately about 0.125 inches. A slot 70 projects through the cylindrical portion 82 along a diameter of the portion 82 that may range from approximately 0.080 inches to 0.120 inches in depth, and from 0.030 inches to 0.070 inches in width. Turning now to FIGS. 5 and 7, a second end 50 of the spool 46 will now be described. Referring first to FIG. 5, the second end 50 has a cylindrical portion 88 that abuts the cylindrical center portion 80 to form a shoulder 86. The cylindrical portion 88 may have a diameter that ranges from approximately about 0.180 inches to approximately about 0.290 inches, and a length of approximately about 0.030 inches to approximately about 0.060 inches. Projecting outwardly from the cylindrical portion 88 is a central cylindrical portion 89 that has a pair of engagement tabs 76 extending radially outwardly from the central portion 89, as best seen in FIG. 7. The central portion 89 has a diameter that may range between approximately 0.150 inches and 0.180 inches, and has a length that varies between approximately about 0.100 inches and 0.130 inches. The engagement tabs 76 may have a radial width of between approximately from 0.010 inches to 0.040 inches from the surface of the central portion 89, a thickness of between approximately 0.030 inches and 0.060 inches, and a length of between approximately 0.080 to approximately about 0.120 inches. The take-up spool 46 may be comprised of any rigid material including various thermoplastics, such as polystyrene, acrylonitrile-butadiene-styrene (ABS), nylon or an acetal resin, such as DELRIN®, which is available from the E.I. DuPont de Nemours and Co. of Wilmington, Del., although other alternatives exist.

Figure 8:
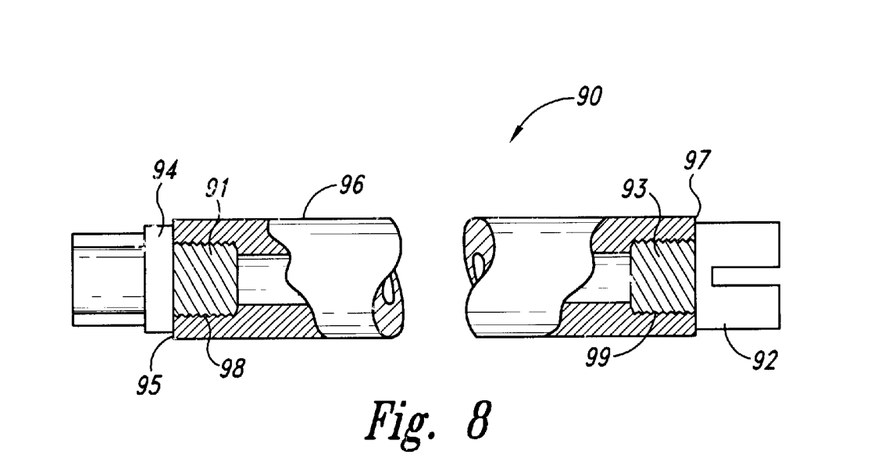
FIG. 8 is a side view of a spool for retaining the transparent film according to another embodiment of the invention.

FIG. 8 is a side view of a take-up spool 90 for retaining the transparent film according to another embodiment of the invention. The spool 90 has a cylindrical center portion 96 with opposing ends 95 and 97 with bores 91 and 93 projecting inwardly into the center portion 96. The bores 91 and 93 have internal threads 98 and 99, respectively. The internal threads 98 and 99 permit engagement ends 92 and 94 to be threadably coupled to the cylindrical center portion 96, thus allowing a variety of different engagement ends to be used with the take-up spool 90.

Figure 9:
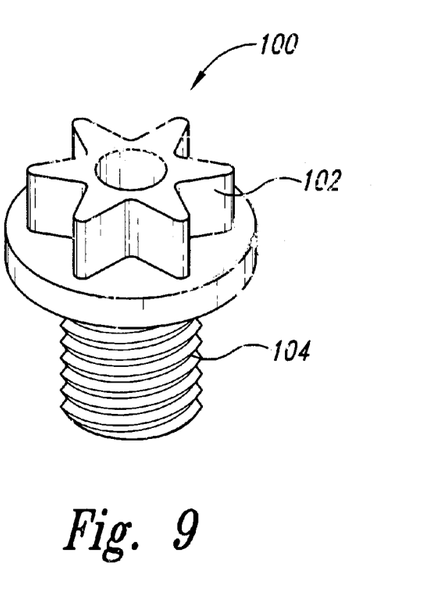
FIG. 9 is an isometric view of an engagement end for a spool according to still another embodiment of the invention.
Figure 10:
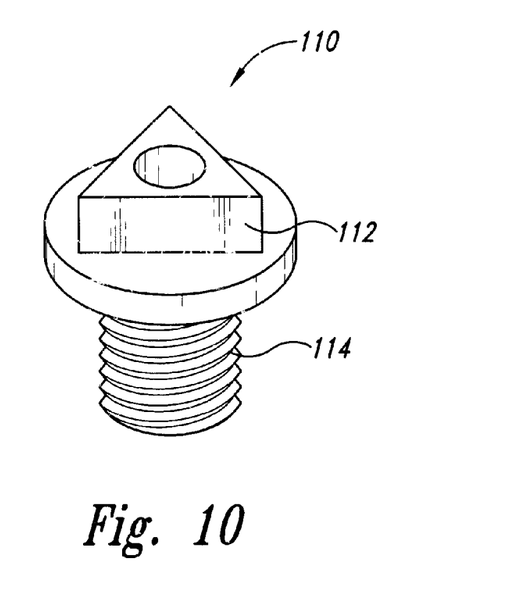
FIG. 10 is an isometric view of an engagement end for a spool according to still another embodiment of the invention.
Figure 11:
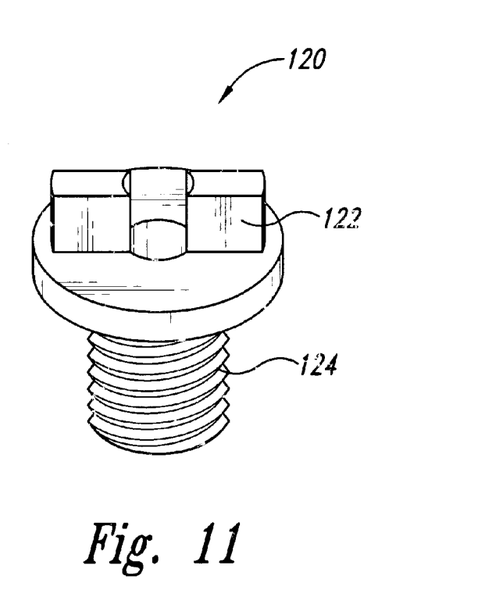
FIG. 11 is an isometric view of an engagement end for a spool according to a further embodiment of the invention.

Turning now to FIGS. 9, 10 and 11, various engagement ends that may be employed with the take-up spool 90 are shown. FIG. 9 shows an engagement end 100 that has an involute spline portion 102 that is attached to a threaded portion 104. FIG. 10 shows an engagement end 110 that has an engagement portion 112 that is of equilateral shape that projects outwardly from a threaded portion 114. Finally, FIG. 11 shows an engagement end 120 having a pair of upwardly projecting tabs 122 that are attached to a threaded portion 124. Still other shapes are possible for the engagement portion of the engagement ends shown in FIGS. 9, 10 and 11. For example, square, or hexagonal shapes may be employed.

The various embodiments of the invention as discussed above advantageously permit the interchangeability of replacement transparent film assemblies in goggles that use protective transparent films in the manner described. Interchangeability is promoted since a film assembly with a single take-up spool that has different spool ends, each being structured to engage a different film advancing mechanism in a different goggle, may be used in both goggles by simply and conveniently selecting the proper end for engagement into the film advancing mechanism. Further, when the take-up spool is threadably coupled to various end-mounted engagement portions, as described above, a single transparent film assembly is adaptable to a wide variety of different film advancing mechanisms that may be present in different models of protective goggles. The practice of the foregoing invention is anticipated to lead to a general reduction in the cost of producing and marketing goggles with renewable surfaces by limiting production of the take-up spools to a few, or even a single type, and through a general inventory reduction.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled in the relevant art will realize. Moreover, the various embodiments described above can be combined to provide further embodiments. Accordingly, the invention is not limited by the disclosure, but instead the scope of the invention is to be determined entirely by the following claims.

What is claimed:

1. A film assembly for providing a renewable viewing surface for a goggle having a lens, comprising:

a transparent film having a length;

a supply spool structured to dispense an unused portion of the length of the transparent film, the spool having a first spool end and a second spool end opposite the first spool end and adapted to be received by a supply magazine attached to a first side of the lens; and a take-up spool structured to receive a spent portion of the length of the transparent film, the spool having a first spool end and a second spool end opposite the first spool end, the first spool end adapted to be engageably received by a film advancing mechanism in a take-up magazine in a first group of goggles including a film advance drive member having a first shape, and the second spool end adapted to be engageably received by a film advancing mechanism in a take-up magazine in a second group of goggles including a film advance drive member having a second shape that is different from the first shape, the first and second groups having the take-up magazine attached to a second side of the lens opposite the first side.

2. The film assembly of claim 1 wherein the first end of the take-up spool is further comprised of a plurality of first coupling elements and the film advance drive member of the first group is further comprised of a plurality of second coupling elements, the first and second coupling elements having complementary mating portions for coupling to one another.

3. The film assembly of claim 2 wherein the first and second coupling elements are further comprised of a plurality of radially and axially extending recesses and protrusions.

4. The film assembly of claim 3 wherein the first coupling elements are comprised of a slot that projects through a diameter of the take-up spool.

5. The film assembly of claim 4 wherein the slot is of rectangular cross sectional shape, having a depth of approximately about 0.08 inches to approximately about 0.12 inches, and a width of approximately about 0.03 inches to approximately about 0.07 inches.

6. The film assembly of claim 3 wherein the first coupling elements are comprised of a central cylindrical portion with a plurality of tabs extending radially outwardly therefrom.

7. The film assembly of claim 6 wherein the central cylindrical portion has a diameter of approximately about 0.18 inches to approximately about 0.29 inches.

8. The film assembly of claim 6 wherein the plurality of tabs is further comprised of a pair of tabs substantially aligned with a diameter of the central cylindrical portion.

9. The film assembly of claim 8 wherein the tabs have a width of approximately about 0.01 inches to approximately about 0.04 inches.

10. The film assembly of claim 1 wherein the second end of the take-up spool is further comprised of a plurality of first coupling elements and the film advance drive member of the second group is further comprised of a plurality of second coupling elements, the first and second coupling elements having complementary mating portions for coupling to one another.

11. The film assembly of claim 10 wherein the first and second coupling elements are further comprised of a plurality of radially and axially extending recesses and protrusions.

12. The film assembly of claim 11 wherein the first coupling elements are comprised of a slot that projects through a diameter of the take-up spool.

13. The film assembly of claim 12 wherein the slot is of rectangular cross sectional shape, having a depth of approximately about 0.08 inches to approximately about 0.12 inches, and a width of approximately about 0.03 inches to approximately about 0.07 inches.

14. The film assembly of claim 10 wherein the first coupling elements are comprised of a central cylindrical portion with a plurality of tabs extending radially outwardly therefrom.

15. The film assembly of claim 14 wherein the central cylindrical portion has a diameter of approximately about 0.18 inches to approximately about 0.29 inches.

16. The film assembly of claim 15 wherein the plurality of tabs is further comprised of a pair of tabs substantially aligned with a diameter of the central cylindrical portion.

17. The film assembly of claim 16 wherein the tabs have a width of approximately about 0.01 inches to approximately about 0.04 inches.

18. The film assembly of claim 1 wherein the supply spool is further comprised of a cylindrical center portion that is structured to retain an unused portion of the transparent film, and the take-up spool is further comprised of a cylindrical center portion structured to retain a spent portion of the transparent film.

19. The film assembly of claim 18 wherein the center cylindrical portion has a diameter of approximately about 0.2 inches and approximately about 0.3 inches.

20. The film assembly of claim 18 wherein the first and second ends are integrally formed with the cylindrical center portion.

21. The film assembly of claim 1 wherein the supply spool and the take-up spool are further comprised of a center cylindrical portion with a first end and an opposing second end, the ends each having a concentric, axial bore projecting inwardly from the ends, the bores being adapted to couple with an engagement end.

22. The film assembly of claim 21 wherein the bores are internally threaded and adapted to accept a threaded engagement end.

23. The film assembly of claim 1 wherein the supply spool and the take-up spool are further comprised of a polymer.

24. The film assembly of claim 23 wherein the polymer further comprises polystyrene.

25. The film assembly of claim 23 wherein the polymer further comprises acrylonitrile-butadiene-styrene (ABS).

26. The film assembly of claim 23 wherein the polymer further comprises nylon.

27. The film assembly of claim 23 wherein the polymer further comprises an acetal resin.

28. A film assembly for a plurality of goggles having a renewable viewing surface and forming at least first and second distinct groups, the goggles of the at least first and second groups further having a lens, a supply magazine at a first side of the lens adapted to dispense an unused portion of a transparent film, and a take-up magazine with a film advancing mechanism coupled thereto that is adapted to receive a used portion of the transparent film, the assembly further including a spool, comprising:

a cylindrical center portion having a first end and an opposing second end, the center portion being structured to retain a portion of the transparent film;

a first spool end coupled to the first end of the center portion, the first spool end being structured to be engageably received by the film advancing mechanism in a take-up magazine in the first group of goggles and the second spool end being structured to be rotatably received in the take-up magazine in the first group of goggles; and a second spool end coupled to the second end of the center portion, the second spool end structured to be engageably received by the film advancing mechanism in a take-up magazine in the second group of goggles and the first spool end being structured to be rotatably received in the take-up magazine in the second group of goggles.

29. The film assembly of claim 28 wherein the first spool end is further comprised of a plurality of first coupling elements and the film advancing mechanism of the first group is further comprised of a plurality of second coupling elements, the first and second coupling elements having complementary mating portions for coupling to one another.

30. The film assembly of claim 29 wherein the first and second coupling elements are further comprised of a plurality of radially and axially extending recesses and protrusions.

31. The film assembly of claim 30 wherein the first coupling elements are comprised of a slot that projects through a diameter of the first spool end.

32. The film assembly of claim 31 wherein the slot is of rectangular cross sectional shape, having a depth of approximately about 0.08 inches to approximately about 0.12 inches, and a width of approximately about 0.03 inches to approximately about 0.07 inches.

33. The film assembly of claim 29 wherein the first coupling elements are comprised of a central cylindrical portion with a plurality of tabs extending radially outwardly therefrom.

34. The film assembly of claim 33 wherein the central cylindrical portion has a diameter of approximately about 0.18 inches to approximately about 0.29 inches.

35. The film assembly of claim 34 wherein the plurality of tabs is further comprised of a pair of tabs substantially aligned with a diameter of the central cylindrical portion.

36. The film assembly of claim 35 wherein the tabs have a width of approximately about 0.01 inches to approximately about 0.04 inches.

37. The film assembly of claim 28 wherein the second spool end is further comprised of a plurality of first coupling elements and the film advancing mechanism of the second group is further comprised of a plurality of second coupling elements, the first and second coupling elements having complementary mating portions for coupling to one another.

38. The film assembly of claim 37 wherein the first and second coupling elements are further comprised of a plurality of radially and axially extending recesses and protrusions.

39. The film assembly of claim 38 wherein the first coupling elements are comprised of a slot that projects through a diameter of the second spool end.

40. The film assembly of claim 39 wherein the slot is of rectangular cross sectional shape, having a depth of approximately about 0.08 inches to approximately about 0.12 inches, and a width of approximately about 0.03 inches to approximately about 0.07 inches.

41. The film assembly of claim 37 wherein the first coupling elements are comprised of a central cylindrical portion with a plurality of tabs extending radially outwardly therefrom.

42. The film assembly of claim 41 wherein the central cylindrical portion has a diameter of approximately about 0.18 inches to approximately about 0.29 inches.

43. The film assembly of claim 42 wherein the plurality of tabs is further comprised of a pair of tabs substantially aligned with a diameter of the central cylindrical portion.

44. The film assembly of claim 43 wherein the tabs have a width of approximately about 0.01 inches to approximately about 0.04 inches.

45. The film assembly of claim 28 wherein the first and second spool ends are integrally formed with the cylindrical center portion.

46. The film assembly of claim 28 wherein the spool is comprised of a polymer.

47. The film assembly of claim 46 wherein the polymer further comprises polystyrene.

48. The film assembly of claim 46 wherein the polymer further comprises acrylonitrile-butadiene-styrene (ABS).

49. The film assembly of claim 46 wherein the polymer further comprises nylon.

50. The film assembly of claim 46 wherein the polymer further comprises an acetal resin.

51. A film assembly for a plurality of goggles forming at least first and second distinct groups, the goggles having a renewable viewing surface and having a lens, a supply magazine at a first side of the lens adapted to dispense an unused portion of a transparent film, and a take-up magazine with a film advancing mechanism coupled thereto that is adapted to receive a used portion of the transparent film, the assembly further including a spool, comprising:

a first spool end structured to be engageably received by the film advancing mechanism in a take-up magazine in the first group of goggles;

a second spool end structured to be engageably received by the film advancing mechanism in a take-up magazine in the second group of goggles; and a cylindrical center portion structured to retain at least a portion of the transparent film having a first end structured to removably receive the first spool end, and an opposing second end structured to removably receive the second spool end.

52. The film assembly of claim 51 wherein the first spool end is further comprised of a plurality of first coupling elements and the film advancing mechanism of the first group is further comprised of a plurality of second coupling elements, the first and second coupling elements having complementary mating portions for coupling to one another.

53. The film assembly of claim 52 wherein the first and second coupling elements are further comprised of a plurality of radially and axially extending recesses and protrusions.

54. The film assembly of claim 53 wherein the first coupling elements are comprised of a slot that projects through a diameter of the first spool end.

55. The film assembly of claim 54 wherein the slot is of rectangular cross sectional shape, having a depth of approximately about 0.08 inches to approximately about 0.12 inches, and a width of approximately about 0.03 inches to approximately about 0.07 inches.

56. The film assembly of claim 55 wherein the first coupling elements are comprised of a central cylindrical portion with a plurality of tabs extending radially outwardly therefrom.

57. The film assembly of claim 56 wherein the central cylindrical portion has a diameter of approximately about 0.18 inches to approximately about 0.29 inches.

58. The film assembly of claim 57 wherein the plurality of tabs is further comprised of a pair of tabs substantially aligned with a diameter of the central cylindrical portion.

59. The film assembly of claim 58 wherein the tabs have a width of approximately about 0.01 inches to approximately about 0.04 inches.

60. The film assembly of claim 51 wherein the second spool end is further comprised of a plurality of first coupling elements and the film advancing mechanism of the second group is further comprised of a plurality of second coupling elements, the first and second coupling elements having complementary mating portions for coupling to one another.

61. The film assembly of claim 60 wherein the first and second coupling elements are further comprised of a plurality of radially and axially extending recesses and protrusions.

62. The film assembly of claim 61 wherein the first coupling elements are comprised of a slot that projects through a diameter of the second spool end.

63. The film assembly of claim 62 wherein the slot is of rectangular cross sectional shape, having a depth of approximately about 0.08 inches to approximately about 0.12 inches, and a width of approximately about 0.03 inches to approximately about 0.07 inches.

64. The film assembly of claim 63 wherein the first coupling elements are comprised of a central cylindrical portion with a plurality of tabs extending radially outwardly therefrom.

65. The film assembly of claim 64 wherein the central cylindrical portion has a diameter of approximately about 0.18 inches to approximately about 0.29 inches.

66. The film assembly of claim 65 wherein the plurality of tabs is further comprised of a pair of tabs substantially aligned with a diameter of the central cylindrical portion.

67. The film assembly of claim 66 wherein the tabs have a width of approximately about 0.01 inches to approximately about 0.04 inches.

68. The film assembly of claim 51 wherein the first and second spool ends and the cylindrical center portion are comprised of a polymer.

69. The film assembly of claim 68 wherein the polymer further comprises polystyrene.

70. The film assembly of claim 68 wherein the polymer further comprises acrylonitrile-butadiene-styrene (ABS).

71. The film assembly of claim 68 wherein the polymer further comprises nylon.

72. The film assembly of claim 68 wherein the polymer further comprises an acetal resin.

73. The film assembly of claim 51 wherein the first and second ends of the center cylindrical portion are further comprised of a concentric, axial bore projecting inwardly from the each end, the bores being adapted to removably mate with the first and second spool ends.

74. The film assembly of claim 73 wherein the bores are further comprised of bores with internal threads.

75. The film assembly of claim 74 wherein the first and second spool ends are further comprised of threaded portions adapted to received by the internal threads in the bores.

76. A film assembly, comprising:
  a spool being adapted for use with a goggles having a transparent lens, the spool comprising:
    an elongated center portion;
    a first spool end formed at a first end of the elongated center portion, the first spool end having formed therein a transverse slot open at one end of the spool; and
    a second spool end formed at a second end of the elongated center portion, the second end being opposite the first end, the second spool end having formed therein at least one transversely extending projection; and
  a length of flexible, transparent film wrapped around the elongated center portion of the spool.

77. The film assembly of claim 76 wherein the elongated center portion has a cylindrical shape.

78. The film assembly of claim 76 wherein the elongated center portion has a diameter of between approximately 0.18 inches and approximately 0.29 inches.

79. The film assembly of claim 76 wherein the slot has a rectangular cross-sectional shape, a depth of between approximately 0.08 inches and approximately 0.12 inches, and a width of between approximately 0.03 inches and approximately 0.07 inches.

80. The film assembly of claim 76 wherein the second spool end has formed therein a plurality of equally spaced transversely extending projections.

81. The film assembly of claim 80 wherein the projections extend beyond the periphery of the elongated center portion by a distance of between approximately 0.01 inches and approximately 0.04 inches.

82. A method of using a film assembly with either a goggle of a first type having a film take-up magazine including a film advance mechanism having a blade projecting upwardly from the lower end of the take-up magazine that is rotatable to draw film into the magazine or a goggle of a second type having a film take-up magazine including a film advance mechanism having a splined recess at the lower end of the take-up magazine opening upwardly into the take-up magazine, the method comprising:
  providing a spool having an elongated center portion with a transverse slot formed at a first end and at least one transversely extending projection formed at a second end;
  if the spool is to be used with a goggle of the first type, inserting the spool in the film take-up magazine with the first end of the spool positioned at the lower end of the take-up magazine and the second end of the spool positioned at the upper end of the take-up magazine; and
  if the spool is to be used with a goggle of the second type, inserting the spool in the film take-up magazine with the first end of the spool positioned at the upper end of the take-up magazine and the second end of the spool positioned at the lower end of the take-up magazine.

83. A method of using a length of transparent film with either a goggle of a first type having a film take-up magazine including a film advance mechanism having a blade projecting upwardly from the lower end of the take-up magazine that is rotatable to draw film into the magazine or a goggle of a second type having a film take-up magazine including a film advance mechanism having a splined recess at the lower end of the take-up magazine opening upwardly into the take-up magazine, the goggles of both the first and second type further having a film supply magazine and a transparent lens positioned between the film supply magazine and the film take-up magazine, the method comprising:
  providing a first spool having an elongated center portion with a transverse slot formed at a first end and at least one transversely extending projection formed at a second end, the first spool having wound thereon a length of transparent film;
  providing a second spool having an elongated center portion with a transverse slot formed at a first end and at least one transversely extending projection formed at a second end;
  inserting the first spool in the film supply magazine;
  if the goggle is of the first type, inserting the second spool in the film take-up magazine with the first end of the second spool positioned at the lower end of the take-up magazine and the second end of the second spool positioned at the upper end of the take-up magazine;
  if the goggle is of the second type, inserting the second spool in the film take-up magazine with the first end of the second spool positioned at the upper end of the take-up magazine and the second end of the second spool positioned at the lower end of the take-up magazine;
  attaching the transparent film to the second spool so the transparent film can wind around the second spool;
  actuating the film advance mechanism to unwind the transparent film from the first spool and wind the transparent film on the second spool until substantially all of the transparent film has been unwound from the first spool;
  removing the first spool from the film supply magazine and the second spool from the film take-up magazine;
  providing a third spool having an elongated center portion with a transverse slot formed at a first end and at least one transversely extending projection formed at a second end, the third spool having wound thereon a length of transparent film;
  inserting third first spool in the film supply magazine;
  if the goggle is of the first type, inserting the first spool in the film take-up magazine with the first end of the first spool positioned at the lower end of the take-up magazine and the second end of the first spool positioned at the upper end of the take-up magazine; and if the goggle is of the second type, inserting the first spool in the film take-up magazine with the first end of the first spool positioned at the upper end of the take-up magazine and the second end of the first spool positioned at the lower end of the take-up magazine.

* * * * *

UNITED STATES PATENT AND TRADEMARK OFFICE
CERTIFICATE OF CORRECTION

PATENT NO.      : 6,416,177 B1                                              Page 1 of 1
DATED           : July 9, 2002
INVENTOR(S)     : George N. Gibson It is certified that error appears in the above-identified patent and that said Letters Patent is hereby corrected as shown below:

Column 2,
Line 65, reads "is comprised of spool" should read -- is comprised of a spool --

Column 4,
Line 65, reads "FIG. 4 has film" should read -- FIG. 4 has a film --

Column 6,
Line 8, reads "For example, square, or" should read -- For example, square or --

Column 11,
Line 20, reads "from the each end," should read -- from each end, --
Line 26, reads "adapted to received by" should read -- adapted to be received by --

Column 12,
Line 65, reads "inserting third first spool" should read -- inserting the third spool --

Signed and Sealed this

Thirteenth Day of May, 2003

JAMES E. ROGAN
*Director of the United States Patent and Trademark Office*